(12) United States Patent
Beaton et al.

(10) Patent No.: US 8,808,256 B2
(45) Date of Patent: Aug. 19, 2014

(54) EYE DRUG DELIVERY SYSTEM

(75) Inventors: Stephen R. Beaton, Jacksonville, FL (US); Michael Ferran, Jacksonville, FL (US); Justin Scott Jacobs, Jacksonville, FL (US); Jason M. Tokarski, Jacksonville, FL (US); Christopher S. Gudeman, Lompoc, CA (US); Fardad Chamran, Mountain View, CA (US); Paul J. Rubel, Santa Barbara, CA (US); Bret A. Coldren, Vista, CA (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 265 days.

(21) Appl. No.: 13/350,963

(22) Filed: Jan. 16, 2012

(65) Prior Publication Data

US 2013/0184661 A1    Jul. 18, 2013

(51) Int. Cl.
| | |
|---|---|
| *A61M 35/00* | (2006.01) |
| *A61F 9/00* | (2006.01) |
| *A61F 9/007* | (2006.01) |
| *A61F 2/14* | (2006.01) |

(52) U.S. Cl.
CPC ........... *A61F 9/0017* (2013.01); *A61F 9/00772* (2013.01)
USPC ....................................... 604/290

(58) Field of Classification Search
CPC ........... A61F 9/00; A61F 11/00; A61F 9/007; A61F 9/0017; A61F 9/00772; A61K 9/0048; A61K 9/0051

USPC .......... 604/8, 9, 10, 264, 289, 290, 294, 500, 604/540, 541, 19, 48, 93.01–99.03; 424/422–428; 623/4.1
See application file for complete search history.

(56) References Cited

U.S. PATENT DOCUMENTS

| | | |
|---|---|---|
| 3,949,750 A | 4/1976 | Freeman |
| 4,573,774 A | 3/1986 | Sitterle |
| 4,869,587 A | 9/1989 | Breger |
| 5,053,030 A | 10/1991 | Herrick et al. |
| 5,171,270 A | 12/1992 | Herrick |
| 5,283,063 A | 2/1994 | Freeman |
| 5,417,651 A | 5/1995 | Guena et al. |
| 5,423,777 A | 6/1995 | Tajiri et al. |

(Continued)

FOREIGN PATENT DOCUMENTS

| | | |
|---|---|---|
| EP | 1734398 B1 | 3/2013 |
| WO | WO 98/53360 A1 | 11/1998 |

(Continued)

OTHER PUBLICATIONS

Search Report mailed Jul. 29, 2013 from Singapore Patent Office for Patent Application No. SG201300067-4.

(Continued)

*Primary Examiner* — Philip R Wiest
(74) *Attorney, Agent, or Firm* — Carl J. Evens

(57) ABSTRACT

A punctal plug or lacrimal insert comprising a microelectromechanical system pump and associated reservoir may be utilized to deliver precise dosages of an active agent into the eye though the tear film. The microelectromechanical system pump comprises four main components; namely, a reservoir, a pump, a series of valves and a vent. The microelectromechanical system pump is positioned within a cavity in the punctal plug. The microelectromechanical system pump is positioned with a cavity in the punctal plug.

9 Claims, 4 Drawing Sheets

(56) References Cited

U.S. PATENT DOCUMENTS

| | | |
|---|---|---|
| 5,723,005 A | 3/1998 | Herrick |
| 5,962,548 A | 10/1999 | Vanderlaan et al. |
| 6,020,445 A | 2/2000 | Vanderlaan et al. |
| 6,099,852 A | 8/2000 | Jen |
| 6,196,993 B1 * | 3/2001 | Cohan et al. ............... 604/891.1 |
| 6,367,929 B1 | 4/2002 | Maiden et al. |
| 6,822,016 B2 | 11/2004 | McCabe et al. |
| 2002/0021410 A1 | 2/2002 | Ye et al. |
| 2005/0119737 A1 * | 6/2005 | Bene et al. ..................... 623/4.1 |
| 2006/0055884 A1 | 3/2006 | Molinari et al. |
| 2006/0279695 A1 | 12/2006 | Ezekiel |
| 2010/0243100 A1 | 9/2010 | Tokarski et al. |
| 2011/0311606 A1 | 12/2011 | Coldren |

FOREIGN PATENT DOCUMENTS

| | | |
|---|---|---|
| WO | WO 00/62760 A1 | 10/2000 |
| WO | WO 2008/011125 A2 | 1/2008 |
| WO | WO 2009/035571 A2 | 3/2009 |

OTHER PUBLICATIONS

U.S. Appl. No. 13/409,210, Coldren et al., Mar. 1, 2012.

International Search Report for corresponding Application No. PCT/US2011/052954 mailed Jan. 16, 2012.

European Search Report dated Mar. 28, 2013 for corresponding Application No. EP13151297.

* cited by examiner

FIG. 1
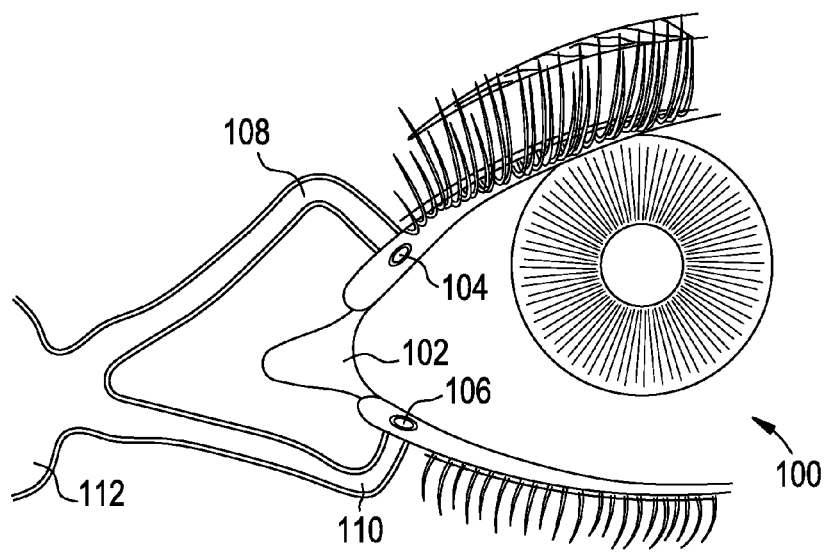
FIG. 2
Prior Art
FIG. 3
Prior Art
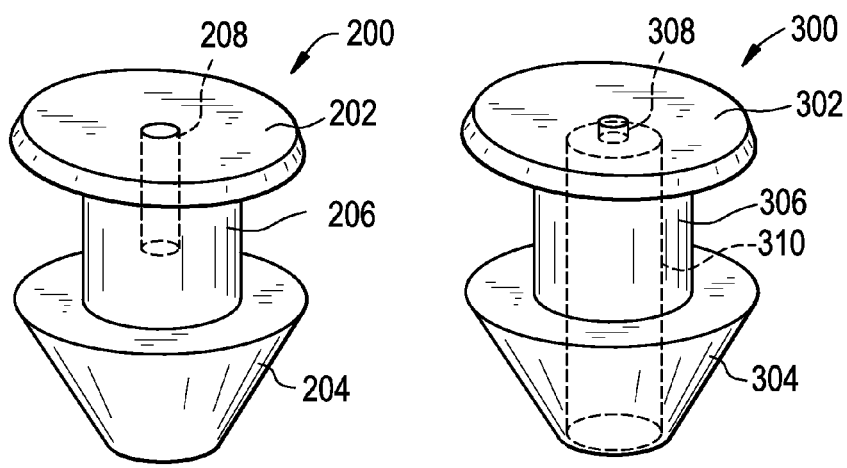

FIG. 4A
FIG. 4B
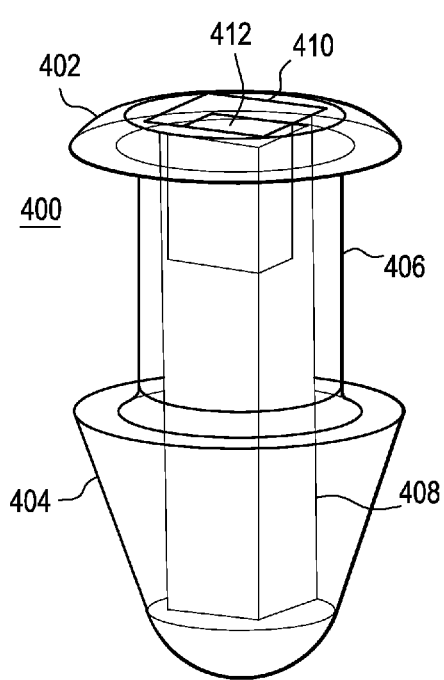
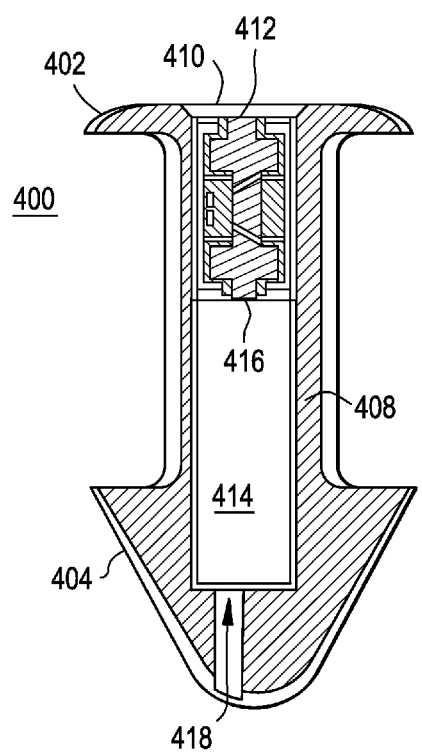

EYE DRUG DELIVERY SYSTEM

BACKGROUND OF THE INVENTION

1. Field of the Invention

The present invention relates to a pulsatile drug release system that is operable to actively pump drug formulations into the eye, and more particularly to a punctal plug comprising a microelectromechanical system (MEMS) pump and associated reservoir.

2. Discussion of the Related Art

The corner of each eye is called a canthus, with the nose side called the nasal canthus and the temporal side called the temporal canthus. At the lower and upper eyelid margins of the nasal canthus are small openings called puncti or puncta. As used herein, both puncti and puncta shall be understood to be the plural form of punctum. Each punctum drains tears from the eyes. A punctal plug or occluder is an ophthalmic device for insertion into a punctum of an eye in order to treat one or more disease states. Typically, a punctal plug is positioned to block tear drainage thereby helping treat dry eyes. Punctal plugs may also be utilized for sustained release of medication to the eye for the treatment of a wide variety of ocular diseases.

In order to treat infection, inflammation, glaucoma, and other ocular diseases, drugs are often required to be administered to the eye. A conventional method of drug delivery is by topical application to the eye's surface. The eye is uniquely suited to this surface route of drug administration because, properly constituted, drugs can penetrate through the cornea, rise to therapeutic concentration levels inside the eye, and exert their beneficial effects. In practice, eye drops currently account for more than ninety-five (95) percent of drug delivery methods for the eye. Rarely are drugs for the eye administered orally or by injection, either because they reach the eye in too low a concentration to have the desired pharmacological effect, or because their use is complicated by significant systemic side effects.

Eye drops, though effective, are unrefined and inefficient. When an eye drop is instilled in the eye, it typically overfills the conjuctival sac, the pocket between the eye and the eyelids, causing a substantial portion of the drop to be lost due to overflow of the eyelid margin onto the cheek. In addition, a substantial portion of the drop remaining on the ocular surface is washed away by tears into the tear drainage system, thereby diluting the concentration of the drug. Not only is this share of the drug dose lost before it can cross the cornea, but this excess drug may be carried into the nose and throat where it is absorbed into the general circulation, sometimes leading to serious systemic side effects. The small portion of the drug in the eye drop which does penetrate the cornea results in an initial peak tissue concentration, a higher level than is required for the initial pharmacological effect. This tissue concentration then gradually decreases, such that by the time the next eye drop is due, the tissue concentration and the intended pharmacological effect may be too low.

To compound the problems described above, patients often do not use their eye drops as prescribed. Often, this poor compliance is due to an initial stinging or burning sensation caused by the eye drop. Certainly, instilling eye drops in one's own eye can be difficult, in part because of the normal reflex to protect the eye. Older patients may have additional problems instilling drops due to arthritis, unsteadiness, and decreased vision, and pediatric and psychiatric patient populations pose difficulties as well. Accordingly, punctal plugs provide a viable means for solving the problems of reliable and efficient drug delivery to the eye.

Punctal plugs may be of the temporary variety or of the permanent variety. Temporary punctal plugs are usually fabricated from collagen or other similar material and are dissolvable. Temporary punctal plugs may be utilized for short duration treatment or to gauge how an individual will react to having the insert placed, for example, will the device cause excessive tearing. Permanent punctal plugs are for long term use and are removable at any time. Permanent punctal plugs are available in various sizes with the largest size that fits providing maximum effectiveness. Permanent punctal plugs are typically made of silicone rubber.

A punctal plug typically includes a body portion sized to pass through a lacrimal punctum and be positioned within a lacrimal canaliculus of the eyelid. The punctal plug also comprises a collarette connected to the body portion and sized to rest on the exterior of the lacrimal punctum. The term lacrimal punctum and lacrimal canaliculus are often utilized interchangeably; however, as used herein, the punctum means the opening and the canaliculus is the passageway or duct-like pathways that lead to the lacrimal sac. If the punctal plug is used to deliver therapeutic agents to the eye, then the body portion may comprise a reservoir for holding the therapeutic agents and the collarette may comprise an opening in communication with the reservoir through which the therapeutic agents are released.

Elution of a drug from the reservoir of a punctal plug into the eye is a passive process wherein the dose and rate of drug delivery is a function of the drug, for example, viscosity, and the design of the reservoir, for example, the one or more outlets. Other factors may also influence the elution of the drug into the eye. For example, physiological factors, such as tear volume, may affect the elution rate from one patient to another. Environmental factors such as temperature and humidity may affect this rate as well. In certain instances, it may be highly desirable to actively pump the drug from the reservoir in order to achieve extremely accurate dosing. Active pumping is also desirable to achieve non-constant, on/off, and/or programmable drug delivery. Accordingly, there exists a need for a device that may be incorporated into a punctal plug for actively pumping drug formulations into the eye.

SUMMARY OF THE INVENTION

The punctal plug incorporating a microelectromechanical system pump and associated reservoir in accordance with the present invention overcomes the limitations associated with the prior art passive devices as briefly described above.

In accordance with a first aspect the present invention is directed to a lacrimal insert. The lacrimal insert comprising a punctal plug having a cavity therein, and a microelectromechanical pump and reservoir positioned within the cavity of the punctal plug, the microelectromechanical pump being configured to deliver at least one therapeutic dosage of an active agent contained in the reservoir into an eye of a patient on demand.

In accordance with another aspect, the present invention is directed to a method for delivering a therapeutic dosage of an active agent into an eye of a patient. The method comprising implanting a punctal plug having a cavity into a punctum of an eyelid, and activating a microelectromechanical pump positioned within the cavity of the punctal plug to deliver a dose of the therapeutic agent to the eye on demand.

The present invention is directed to a pulsatile drug release system that actively pumps drug formulations, medications and/or active agents into the eye of a living organism. As configured, the system comprises a pump designed to fit into an injection molded silicone plug or lacrimal insert to be inserted into the lower punctum of the eyelid. The pump comprises a microelectromechanical system pump constructed from silicon wafers using traditional bulk micromachining processes and wafer bonding and dicing. The pump may be actuated by cycling a magnetic field in close proximity to the punctum.

The microelectromechanical pump may be configured to deliver small dose quantities of therapeutic agent to the eye. The doses may range from about one (1) to about one-hundred (100) nanoliters of active agent. Each dose would be the result of a series of pump strokes displacing about forty (40) to about one-hundred (100) picoliters with each successive movement of the pump piston. This pump may be fabricated from silicon and glass wafers commonly utilized in the fabrication of semiconductor devices. The pump is actuated with a magnetic field generated by a permanent magnet or an electromagnet. The design of the pump and actuation system are such that a single pulsatile dose may be delivered in less than ten (10) minutes.

The micromechanical pump comprises four main components; namely, a reservoir, a pump, valves and a vent. The reservoir holds approximately one-hundred (100) nanoliters of active agent. The pump itself is a dual acting design whereby the piston is pushed forward by the magnetic field and returns to its home position via a series of springs or biasing means pulling it backwards when the magnetic field is removed. The valves serve to allow fluid to be pumped or drawn from the reservoir into the pump chamber and to open into the eye when the pump is activated. The vent serves to allow air and possibly fluid from the punctum into the reservoir to allow drug formulations to be displaced from the system. Without the vent, the pump may stall or otherwise not displace formulation.

The microelectromechanical system pump of the present invention is an efficient means for delivering precise amounts of active agent directly into the eye through the tear film. The pump is simple to fabricate, made from materials that are suitable for human implantation and reliable and easy to utilize. When the reservoir is empty, the device may be thrown away and replaced.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 1 illustrates the anatomy of the lacrimal drainage system of the human eye.

FIG. 2 illustrates an example of a conventional punctal plug that is known in the art.

FIG. 3 illustrates an example of a punctal plug, including a reservoir for the release of one or more therapeutic agents, that is known in the art.

FIGS. 4A and 4B are diagrammatic illustrations of an exemplary punctal plug comprising a microelectromechanical system pump in accordance with the present invention.

DETAILED DESCRIPTION OF THE PREFERRED EMBODIMENTS

Figure 5A:
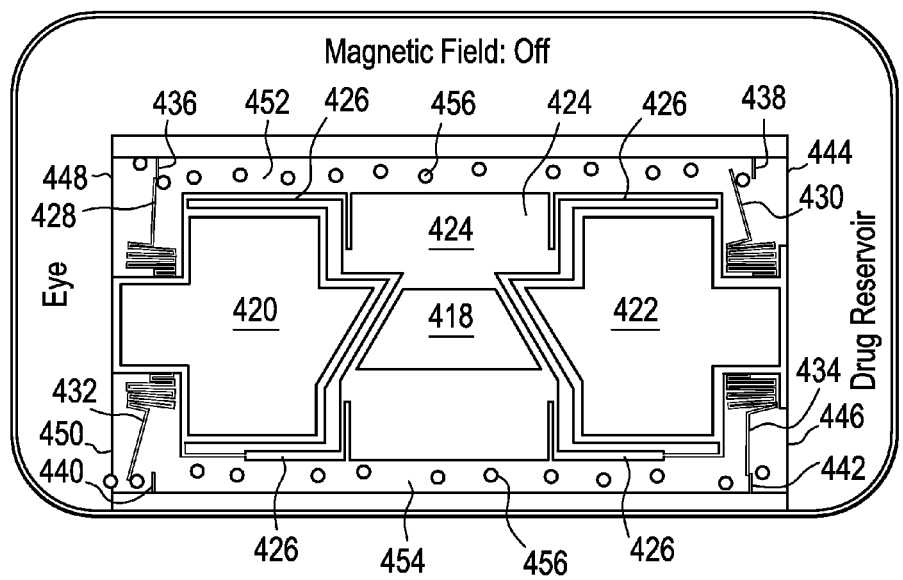
FIG. 5 is a diagrammatic illustration of an exemplary microelectromechanical system pump in accordance with the present invention.

FIG. 1 illustrates the anatomy of the drainage system of a human eye 100. Tears are produced by the lacrimal gland, not illustrated, superior to the outer portion of each eye 100. Tears flow across the surface of the eye 100 to a shallow pool, termed the lacrimal lake 102, located where the upper and lower eyelids come together at their inner ends or nasal ends. From there, the tears drain through small openings in each of the eyelids, namely, the upper lacrimal punctum 104 and the lower lacrimal punctum 106. From the upper lacrimal punctum 104 and the lower lacrimal punctum 106, the tears pass into the upper lacrimal canaliculus 108 and lower lacrimal canaliculus 110, respectively, which are duct-like pathways leading to the lacrimal sac 112. The lacrimal sac 112 is the superior, expanded portion of the nasolacrimal duct, not illustrated, which drains tears into the nasal system. The upper lacrimal punctum 104 and associated canaliculus 108 typically only drain about ten percent of the tears from the eye 100, such that their obstruction virtually never leads to the tear overflow.

Tears or the tear film comprises three layers. The first layer or bottom layer is the layer that coats the eye and comprises mucin which is created by cells in the conjunctiva referred to as goblet cells. The mucin fills in microscopic irregularities on or in the eye's surface which is important to clear vision. The second layer or middle layer of the tear film comprises essentially water and makes up the bulk of the tear film. A majority of the watery component is produced or supplied from the main lacrimal or tear gland. Emotional tears and reflect tears, i.e. tears resulting from a stimulus such as bright light or a foreign body, come from the main lacrimal gland. Accessory lacrimal glands, known as the glands of Wolfing and Kraus are found in the eyelid tissue and also contribute to the watery component. The third or top layer of the tear film comprises a thin layer of oil secreted by the meibomian glands and functions to prevent the tears from evaporating too quickly.

Insufficient tears, or "dry eye" is a common condition caused by insufficient production of tears from the lacrimal gland which causes symptoms such as dryness, redness, burning, reflex tearing, itching, or foreign body sensation. In especially difficult cases of dry eye, a punctal occluder or punctal plug may be placed into one or both of the lacrimal puncta 104, 106, see FIG. 1. Punctal plugs prevent the tears, which are being produced in deficient volume by the lacrimal glad, from draining into the lacrimal canaliculi 108, 110. Punctal plugs may be secured in the lacrimal puncta without anesthesia and removed with ease when required.

Referring now to FIG. 2, there is illustrated an exemplary punctal plug 200. The punctal occluder or plug 200 comprises a collarette 202 which is configured to rest on the exterior of the punctum 104, 106 (FIG. 1), a bulb 204 that blockingly projects into the canaliculus 108, 110 (FIG. 1), and a body portion 206 connecting the collarette 202 and the bulb 204. Commercially available punctal plugs usually have a length of approximately 2.0 millimeters, and differ from each other only slightly in configuration. For example, the bulbs of the punctal plugs are designed to prevent the plug from being easily dislodged from the canaliculus, and may be tapered for ease of insertion into the puncta. The collerette is designed to have a diameter sufficient to prevent the plug from completely entering the canaliculus, and are preferably smooth to minimize irritation of the eye. The body portions of different punctal plugs are also similar in design and are essentially a non-functional connection between the collarette and the bulb portions. The collarette 202 may include an aperture 208, illustrated in phantom, extending into the body portion 206 to aid in grasping or securing the punctal plug 200 during its insertion into the puncta. Examples of punctal plugs may be found in U.S. Pat. Nos. 3,949,750 and 5,283,063 to Freeman, U.S. Pat. Nos. 5,053,030, 5,171,270 and 5,723,005 to Herrick, U.S. Pat. No. 5,417,651 to Guena et al. and U.S. Pat. No. 5,423,777 to Tajiri et al.

In addition to, or alternately, a punctal occluder or plug may be utilized to deliver one or more therapeutic agents and/or medications. FIG. 3 illustrates an ophthalmic insert or punctal plug 300 that adapts the form of a conventional punctal plug 200, as illustrated in FIG. 2, to incorporate a reservoir 310, illustrated in phantom, designed to store and release medication onto the surface of the eye. The reservoir 310 may be configured to release the medication in any number of ways, including pulsatile and continuous. In addition, the reservoir may be refilled as required. As in the previously described exemplary embodiment, the ophthalmic insert or punctal plug 300 comprises a collarette 302, a bulb 304 and a body portion 306. The punctal plug 300 may be molded or otherwise formed from a flexible material, such as silicone, that is impermeable to the medication which will fill the reservoir 310. Although silicone is described herein, it is important to note that any suitable biocompatible material may be utilized. The reservoir 310 may be formed by a channel through the interior of the body portion 306 of the plug 300. In one exemplary embodiment, the body portion 306 may be flexible, or even accordion shape so as to provide the capability of lengthwise expansion as it is filled with medication. The collarette 302 anchors the plug 300 to the exterior of the lacrimal punctum 104 and 106 (see FIG. 1) and may be provided with an opening 308 which is in fluid communication with the reservoir 310. In order to control the delivery of a specific medication, the geometry of the opening 308 may be customized in a variety of ways. For example, the opening 308 may be designed for releasing the medication at a constant sustained release rate, a pulsatile release rate, an exponential release rate and/or any combination thereof. Through opening 308, medication is released from the reservoir 310 into the tears of the lacrimal lake where the medication mixes, as eye drops do, with the tears and penetrate the eye to have the intended pharmacological and therapeutic effect. Although not required, the punctal plug 300 may comprise an enlarged bulb 304 to help secure the plug 300 in position within the canaliculus and also to provide additional volume for the reservoir as illustrated. An exemplary device may be found in U.S. Pat. No. 6,196,993 to Cohan et al.

Punctal plugs may take on any number of configurations, sizes and be formed from any number of materials, depending on the desired functionality and/or medications to be delivered.

As set forth above, punctal plugs may take any size and shape. Typically, the body of the punctal plug is in the shape of an elongated cylinder, and may vary in length in the range from about 0.8 mm to about 5 mm and may vary in width in the range from about 0.2 mm to about 3 mm. The size of the opening for medication or drug release may be in the range from about 1 nm to about 2.5 mm. Rather than one large opening at any one location, multiple small openings may be used. The body of the punctal plug may be wholly or partially transparent or opaque. Optionally, the body may include a tint or pigment that makes the plug easier to see when it is placed in a punctum.

Punctal plugs may be fabricated from any number of suitable biocompatible materials including silicone, silicone blends, silicone co-polymers, for example, hydrophilic monomers of polyhydroxyethylmethacrylate, polyethylene glycol, polyvinylpyrrolidone and glycerol, and silicone hydrogel polymers, for example, those described in U.S. Pat. Nos. 5,962,548, 6,020,445, 6,099,852, 6,367,929, and 6,822,016. Other suitable biocompatible materials include polyurethane, polymethylmethacrylate, poly(ethylene glycol), poly (ethylene oxide), poly(propylene glycol), poly(vinyl alcohol), poly(hydroxyethylmethacrylate), poly(vinylpyrrolidone), polyarcrylic, poly(ethyloxazoline), poly(dimethyl acrylamide), phospholipids, for example, phosphoryl choline derivatives, polysulfobetains, acrylic esters, polysaccharides and carbohydrates, for example, hyaluronic acid, dextran, hydroxyethyl cellulose, hydroxyl propyl cellulose, gellan gum, guar gum, heparin sulfate, chondroitin sulfate, heparin and alginate, proteins, for example, gelatin, collagen, albumin and ovalbunin, polyamino acids, fluorinated polymers, for example, polytetrafluoroethylene and polyvinylidine fluoride, polypropylene, polyethylene, nylon and ethylene-co-vinylacetate.

The exterior surfaces of the punctal plug may be wholly or partially coated with a number of different biocompatible coatings. The coating may provide a number of benefits, including lubriciousness to aid in insertion of the device, muco-adhesiveness to improve tissue compatibility, texture to aid in anchoring the device and/or any combination thereof. Suitable biocompatible coatings include gelatin, collagen, hydroxyethyl methacrylate, poly(vinylpyrrolidone), poly (ethylene glycol), heparin, chondroitin sulfate, hyaluronic acid, synthetic and natural proteins, polysaccharides, thiomens, thiolated derivates of polyacrylic acid and chitosan, polyacrylic acid, carboxymethal cellulose and combinations thereof.

It has been found that with certain therapeutic agents or medications, it may be desirable to create a barrier layer between the therapeutic agent containing material to be released from the reservoir within the punctal plug and the interior surface of the walls that define the reservoir due to possible interactions, or inadvertent leaching of the active therapeutic agent through the wall of the punctal plug. In addition, it has been found that the retention of therapeutic agent within the reservoir may be aided by the selection of the geometric configuration of the punctal plug, or with the addition of various anchoring features. For example, a reservoir may comprise a simple cylindrical configuration which may not securely hold a particular therapeutic agent within the reservoir. In other words, that shape, even with a primer layer or adhesive layer may not be sufficient to hold the agent in place. Accordingly, the geometry of the reservoir may be modified to include protrusions or indents for holding the agent. These geometric variations may be utilized alone or in combination with various barrier layers, adhesives and/or primer layers. In other words, various combinations of geometries and coatings may be utilized to hold the drug in and/or force the drug out as required. For example, a barrier layer may be disposed on the external surface of the punctal plug to inhibit diffusion of the therapeutic agent in the body of the punctal plug and to inhibit the infusion of tears into the reservoir containing the therapeutic agent. In addition, the geometry of the punctal plug may be modified to create a better fit within the canaliculus.

The present invention is directed to a pulsatile drug release system that can actively pump highly-concentrated drug formulations or medications into the eye. The pump and associated reservoir would preferably fit into a reservoir or cavity of a punctal plug which will then be implanted into one or both of the lower punctum of the eyelid and the upper punctum of the eyelid. Preferably, the punctal plug is implanted into the lower punctum of the eyelid. In the exemplary embodiment described herein, the pump may comprise a microelectromechanical system pump constructed from silicon wafers using traditional bulk micromachining processes. The pump may be actuated by cycling a magnetic field in close proximity to the punctum. It is important to note that any suitable microelectrochemical system pump may be utilized to deliver single doses of drugs in the 2-20 nanoliter range with each stoke of the pump ranging in the 0.02-0.50 nanoliter range.

Microelectromechanical structures (MEMS) and other microengineered devices are currently being developed for a variety of applications because of their size, cost and reliability. Many different varieties of MEMS devices and actuators have been created, including switches, valves, microgears, micromotors and other micromachined devices that are capable of motion or applying force. These MEMS devices may be employed in a variety of applications, including hydraulic applications in which MEMS pumps or valves are utilized, and optical applications in which MEMS light valves and shutters are utilized.

MEMS devices have relied upon various techniques to provide the motive force necessary to cause the desired motion within these microstructures. For example, cantilevers have been employed to apply mechanical force in order to rotate micromachined springs and gears. In addition, some micromotors are driven by electromagnetic fields, while other micromachined structures are activated by piezoelectric or electrostatic forces. MEMS devices that are actuated by the controlled thermal expansion of an actuator or other MEMS components have also been developed. These thermal actuators may comprise arched beams formed from silicon or metallic materials or combinations thereof that further arch or otherwise deflect when heated, thereby creating motive force. As an additional example of a type of thermally actuated device, thermal inkjet printing may be considered one of the classic applications of MEMS.

In practically every application of MEMS devices, precisely controlled and reliable movement is required. Given the micron scale dimensions associated with MEMS structures, stable and predictable movement characteristics are important. The movement characteristics of MEMS devices can be affected by intrinsic factors such as the type of materials utilized to fabricate the MEMS device, the dimensions and structure of the MEMS device, and the effects of semiconductor process variations. In addition, the movement characteristics of MEMS devices can be affected by extrinsic factors such as fluctuations in the ambient temperature in which the MEMS device operates. The impact of both the intrinsic and extrinsic factors may vary from device to device. For example, while thermally actuated MEMS devices are affected by all of the above factors, they are particularly sensitive to ambient operating temperature variations. Essentially, unless thermal compensation is built into the device or thermal control is incorporated as part of the device packaging, some types of thermally actuated MEMS devices may operate unpredictably or erroneously since the MEMS device will move not only in response to thermal actuation caused by active heating or cooling, but also due to changes in the ambient operating temperature. Therefore, it would be advantageous to develop other types of thermally actuated structures that would operate more reliably or more precisely even when exposed to significant ambient temperature fluctuations. Numerous applications, including switches, relays, variable capacitors, variable resistors, valves, pumps, optical mirror arrays and electromagnetic attenuators would be better served by MEMS structures with these attributes. However, thermal actuators are utilized when necessary.

Referring now to FIG. 4A, there is illustrated an exemplary punctal plug 400 configured to have mounted therein a microelectromechanical system pump and associated reservoir. The punctal plug 400 comprises a collarette 402, a bulb 404, a body portion 406 and a bore 408 into which the microelectromechanical system pump is mounted. As illustrated, in this exemplary embodiment, the bore 408 extends from the bulb 401 through the body 406 to an opening 410 in the collarette 402 for drug release. The microelectromechanical system 412 pump may be press-fit into the bore 408 of the punctal plug 400 in a manner that prevents the microelectromechanical system pump 412 from protruding from the punctal plug 400, thereby preventing possible irritation to the eye. The MEMS pump 412 may be secured by any suitable means, for example, it may be held in place with an epoxy or other type medical grade adhesive. In this exemplary embodiment, the bore 408 is substantially rectangular; however, any other suitable shape may be utilized.

FIG. 4B is a sectional view of the exemplary punctal plug 400 with the microelectromechanical system pump 412 or MEMS pump 412. The MEMS pump 412 comprises a reservoir component 414 and a pump component 416. The reservoir component 414 is configured to hold one or more drug formulations for release into the eye. At the end opposite the pump component 416, the reservoir component 414 comprises a vent 418. As the MEMS pump 412 is cycled, as explained in detail subsequently, the reservoir component 414 is preferably vented to the atmosphere or ambient environment in order to prevent the pump from stalling. With the vent port 418 placed in the bottom of the punctal plug 400, it may be possible that the reservoir component 414 could possibly backfill with air, tear fluid or even perhaps mucus; however, this backfill would not create a level of fluidic resistance high enough to cause the MEMS pump 412 to stall. The pump component 416 comprises multiple components, explained in detail subsequently, designed to pump one or more doses of medication or drug formulation per day into the eye over an extended period of time, for example, three months. After the three month period is complete, the MEMS pump 412 may be removed and a new one inserted or the entire pump and plug assembly 400 may be replaced.

In the exemplary embodiment illustrated, the MEMS pump 412 may be a substantially rectangular shaped structure with a height of 1.8 mm, and a length and width of 0.4 mm. The reservoir component 414 is preferably designed to accommodate 100 nanoliters of drug or medication and the pump component 416 is preferably designed to pump, with each stroke of the pump, 0.02 nanoliters to about 0.50 nanoliters such that a single dose will be in the range from about 2 to 20 nanoliters. The drug formulation or medication to be pumped into the eye preferably has a viscosity in the range of 1,000 to 5,000 centipoise. However, the MEMS pump 412 may be designed to work with materials having an aqueous viscosity all the way up to a viscosity of 20,000 centipose. These materials may include neat liquids, homogeneous mixtures and also heterogeneous mixtures, including emulsions and suspensions.

The reservoir component 414 may comprise any suitable configuration and may be formed from any suitable biocompatible material suitable for holding drug formulations. The reservoir component 414 may be coated with an agent for maintaining the potency of the drug formulation. The reservoir component 414 may comprise one or more compartments and/or baffles. The reservoir may be designed with features that optimize flow during pumping. One such feature is a baffle design that maintains a fluidic path of constant cross section creating consistent back pressure on the pump. Another possible feature is to round corners inside the reservoir to reduce the amount of fluidic drag on the pump. The surfaces inside the reservoir and pump may also be coated with a hydrophobic or hydrophilic coating as a means to optimize the flow characteristics with the material properties of a given drug formulation. One such example is a hydrophobic or hydrophilic silane treatment.

Figure 5B:
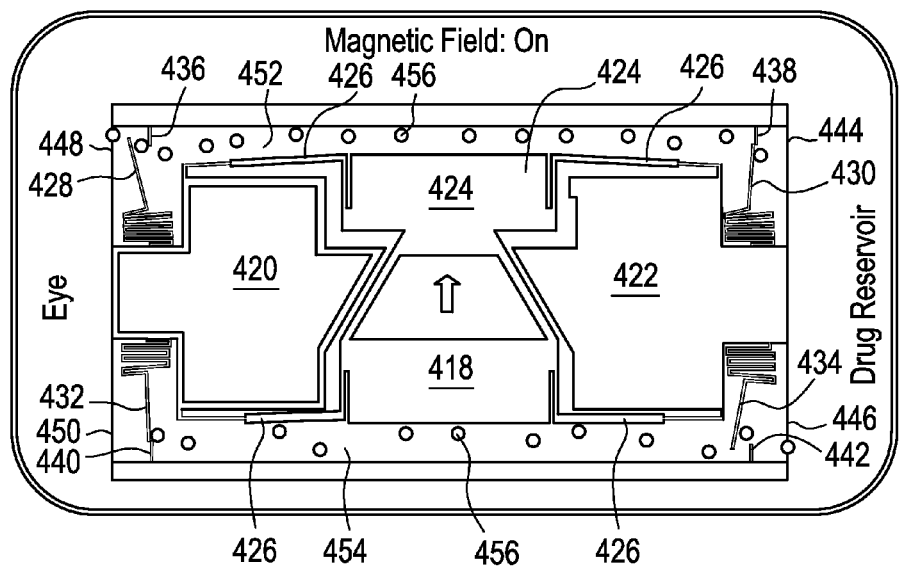

Referring now to FIG. 5, there is illustrated the exemplary pump component 416 in detail. The pump component 416 comprises three pole sections 418, 420 and 422, a piston 424, springs 426 connected to the piston 424, four spring loaded valves 428, 430, 432, 434, four valve seats 436, 438, 440 and 442, two intake ports 444 and 446, two output ports 448 and 450 and two channels 452 and 454. The pump component 416 employs a dual-acting piston 424 with the forward stroke driven by a magnetic field and the reverse stroke driven by the springs 426 attached to the piston 424. When the pump component 416 is subjected to a magnetic field, the field lines pass through the poles 418, 420, and 422 pulling the piston 424 in a direction that drives the drug formulation, illustrated as dots 456, through outlet port 448 via channel 452 by opening valve 428 and closing valve 430, against seat 438. This same action causes valve 432 to close against seat 440 and open valve 434 thereby allowing the drug formulation or medication in the reservoir component 414 to enter channel 454. Once the magnetic field is removed, the springs 426 pull the piston 424 back into its original position to displace the drug formulation in channel 454 by opening valve 432 and closing valve 434 against seat 442. Accordingly, two doses are delivered by cycling a magnetic field. In the rest position, all valves 428, 430, 432 and 434 are closed against seats 436, 438, 440 and 442 respectively. As utilized herein, closed valves mean substantially closed because in fabricating the devices, gaps are inherent in the process; however, these gaps are only 1 to 2 microns and as such represent insignificant leakage. This pumping process is repeated until the total dose has been dispensed. As the dose is dispensed from the outlet ports 448 and 450, it is expected that blinking would cause the tear film to wash the medication or drug formulation into the eye for diffusion of the drug or medication into the eye tissue as set forth above. It must be noted that the design of the valves, valve seats and the piston has been optimized to seal the device as much as possible to prevent passive leaking of the drug into the eye between doses.

Figure 6:
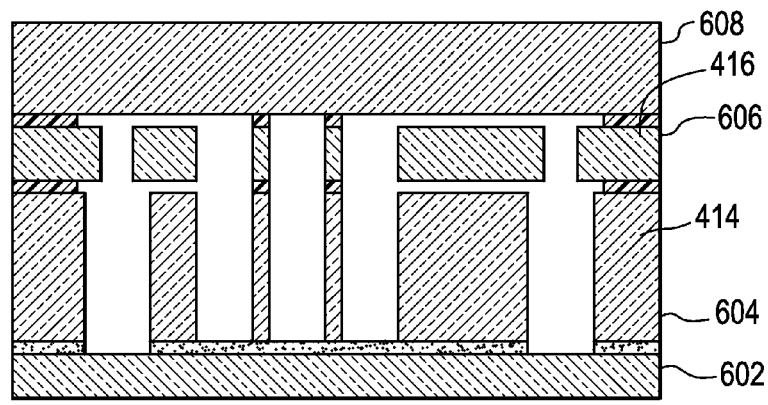
FIG. 6 is a diagrammatic illustration of the physical construction of the microelectromechanical system pump in accordance with the present invention.

The basic construction of the MEMS pump 412 is illustrated in FIG. 6. There are three silicon layers 602, 604 and 606 bonded together that form the basic construct of the reservoir component 414 and the pump component 416. These three silicon layers 602, 604 and 606 are etched using conventional bulk micromachining process then bonded together with a fusion bonding process between layers 602 and 604 and a siloxane-based polymer component between layers 604 and 606 and between layers 606 and layer 608. The primary reason for using the siloxane bonding agent is to create a 1 micro meter gap between the layers thereby providing needed clearance for the components i.e. valves and pistons, residing in layer 606. Layer 608 is a glass cover that is added to the top of the stack so as to provide visibility into the working of the pump component 416 and the reservoir component 414. The base layer 602 is about forty (40) micrometers thick, the reservoir layer 604 is about two hundred seventy (270) micrometers thick, pump layer 606 is about fifty (50) micrometers thick and the glass layer 608 is about forty (40) micrometers thick.

The three pole sections 418, 420 and 422 are silicon portions that have been metalized. The three pole sections 418, 420 and 422 may be metalized with any suitable magnetically conductive material such as a nickel and iron alloy utilizing any metallization technique known in the relevant art. The two end poles 420 and 422 are fixed within the device while the middle pole 418 which is operatively associated with the piston 424 which in turn is connected to the springs 426 or other biasing means. The poles 418, 420 and 422 are designed such that when an applied magnetic field is positioned in proximity to the device, the magnetic field forces the middle pole 418 into the piston 424 as described above. Any suitable means may be utilized to create a pulsatile magnetic field to control the dosing. For example, a permanent magnet that may be pulsed or controlled to create a pulsed magnetic field may be utilized. Alternately, an electromagnet may be utilized. Regardless of the type of device utilized, it is preferably positioned in close proximity to the punctal plug, approximately 5 to 40 microns.

It is important to note that the devices set forth above represent exemplary embodiments of devices and that specific elements may take any number of configurations.

Figure 7:
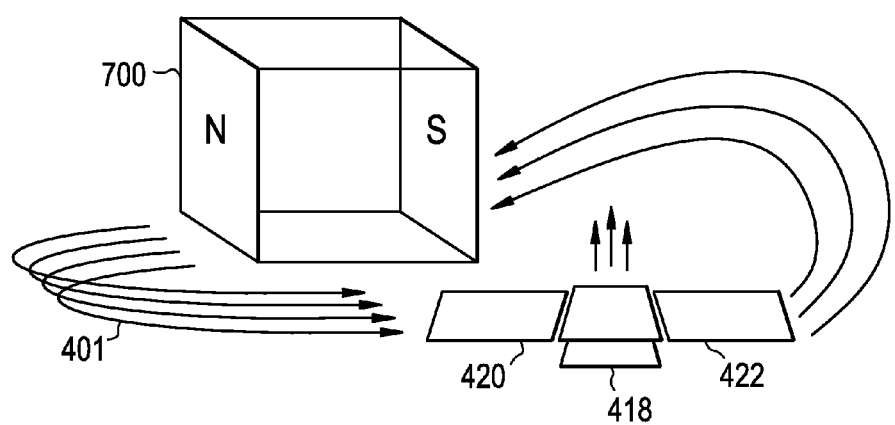
FIG. 7 is a diagrammatic illustration of the interaction of the microelectromechanical system pump and a magnet in accordance with the present invention.

As set forth above, the MEMS pump may be actuated utilizing a magnetic field. FIG. 7 illustrates the basic operation of the MEMS pump relative to a generated magnetic field. Essentially, the MEMS pump may be actuated through a magnetic field, represented by field lines 401, passing parallel through the two nickel-iron clad static poles 420 and 422 and through the nickel-iron clad static pole 418 and piston. The magnetic field 401 may be generated by a permanent magnet 700 such as a rare-earth permanent magnet. The piston/moveable pole and static pole combination described and illustrated herein is configured to take advantage of the fact that when a magnetic field passes through one static pole, the magnetic field desires to take the path of least reluctance to the opposite static pole, that is, when the magnetic field passing through the poles is parallel with respect to the poles. When the magnetic field passes through the first static pole it draws the moveable pole and piston closer to the opposite static pole to create the path of least reluctance, therefore displacing the piston. The piston is returned to its original position when the magnetic field is not strong enough to overcome the spring and fluid resistances when filled. Positive output of drug formulation or medication is achieved by repeating the cycle of applying a strong enough magnetic field to fully displace the position then remove or decrease the magnetic field strength to allow the springs to return the piston to its neutral position. In alternate exemplary embodiments, the MEMS pump may comprise mechanical stops that are configured to precisely control movement of the piston thereby allowing for precise dosing control.

It is important to note that any suitable magnet may be utilized to actuate the pump. Magnets, such as permanent magnets, come in different grades, sizes, shapes, and strengths. The selection of the magnet is determined by a number of factors, including pump size and configuration and the properties of the formulation contained within the reservoir. Depending on function, the pump may be sized and configured accordingly. In addition, the duty cycle of applying and removing the magnetic field could affect pump efficiency. The drug formulation also plays an important role in that different formulations may vary in properties such as viscosity which in turn may affect the size of the pump as well as the strength of the magnet. An electromagnet has an advantage in that the physical spatial location would be fixed and the field strength could be adjusted based on current input to the coil surrounding the core. A permanent magnet would have to be physically moved relative to the pump to change the strength of the magnetic field as field strength is related to distance by the equation $$B \alpha 1/d^2,$$

wherein d is distance.

The exemplary MEMS pump described herein may be used to deliver various drug formulations, medications and/or active agents for the one or more of the treatment, inhibition, and prevention of numerous diseases and disorders. The exemplary MEMS pump may be used to deliver at least one active agent and may be used to deliver different types of active agents. For example, the exemplary MEMS pump may be used to deliver azelastine HCl, emadastine difumerate, epinastine HCl, ketotifen fumerate, levocabastine HCl, olopatadine HCl, pheniramine maleate, and antazoline phosphate for one or more of the treatment, inhibition, and prevention of allergies. The exemplary MEMS pump may be used to deliver mast cell stabilizers, for example, cromolyn sodium, lodoxamide tromethamine, nedocromil sodium, and permirolast potassium.

The exemplary MEMS pump may be used to deliver mydriatics and cycloplegics including atropine sulfate, homatropine, scopolamine HBr, cyclopentolate HCl, tropicamide, and phenylephrine HCl. The exemplary MEMS pump may be used to deliver ophthalmic dyes including rose begal, sissamine green, indocyanine green, fluorexon, and fluorescein.

The exemplary MEMS pump may be used to deliver corticosteroids including dexamethasone sodium phosphate, dexamethasone, fluoromethalone, fluoromethalone acetate, loteprednol etabonate, prednisolone acetate, prednisolone sodium phosphate, medrysone, rimexolone, and fluocinolone acetonide. The exemplary MEMS pump may be used to deliver non-steroidal anti-inflammatory agents including flurbiprofen sodium, suprofen, diclofenac sodium, ketorolac tromethamine, cyclosporine, rapamycin methotrexate, azathioprine, and bromocriptine.

The exemplary MEMS pump may be used to deliver anti-infective agents including tobramycin, moxifloxacin, ofloxacin, gatifloxacin, ciprofloxacin, gentamicin, sulfisoxazolone diolamine, sodium sulfacetamide, vancomycin, polymyxin B, amikacin, norfloxacin, levofloxacin, sulfisoxazole diolamine, sodium sulfacetamide tetracycline, doxycycline, dicloxacillin, cephalexin, amoxicillin/clavulante, ceftriaxone, cefixime, erythromycin, ofloxacin, azithromycin, gentamycin, sulfadiazine, and pyrimethamine.

The exemplary MEMS pump may be used to deliver agents for the one or more of the treatment, inhibition, and prevention of glaucoma including epinephrines, including dipivefrin; alpha-2 adrenergic receptors, including aproclonidine and brimonidine; betablockers including betaxolol, carteolol, levobunolol, metipranolol, and timolol; direct miotics, including carbachol and pilocarpine; cholinesterase inhibitors, including physostigmine and echothiophate; carbonic anhydrase inhibitors, including acetazolamide, brinzolamide, dorzolamide, and methazolamide; prostoglandins and prostamides including latanoprost, bimatoprost, uravoprost, unoprostone cidofovir and travoprost.

The exemplary MEMS pump may be used to deliver antiviral agents, including fomivirsen sodium, foscarnet sodium, ganciclovir sodium, valganciclovir HCl, trifluridine, acyclovir, and famciclovir. The exemplary MEMS pump may be used to deliver local anesthetics, including tetracaine HCl, proparacaine HCl, proparacaine HCl and fluorescein sodium, benoxinate and fluorescein sodium, and benoxnate and fluorexon disodium. The exemplary MEMS pump may be used to deliver antifungal agents, including fluconazole, flucytosine, amphotericin B, itraconazole, and ketocaonazole.

The exemplary MEMS pump may be used to deliver analgesics including acetaminophen and codeine, acetaminophen and hydrocodone, acetaminophen, ketorolac, ibuprofen, and tramadol. The exemplary MEMS pump may be used to deliver vasoconstrictors including ephedrine hydrochloride, naphazoline hydrochloride, phenylephrine hydrochloride, tetrahydrozoline hydrochloride, and oxymetazoline. The exemplary MEMS pump may also be used to deliver vitamins, antioxidants, and nutraceuticals including, vitamins A, D, and E, lutein, taurine, glutathione, zeaxanthin, fatty acids and the like.

The drug formulations, medications and/or active agents delivered by the exemplary MEMS pump may be formulated to comprise excipients including synthetic and natural polymers, including polyvinylalcohol, polyethyleneglycol, PAA (polyacrylic acid), hydroxymethyl cellulose, glycerine, hypromelos, polyvinylpyrrolidone, carbopol, propyleneglycol, hydroxypropyl guar, glucam-20, hydroxypropyl cellulose, sorbitol, dextrose, polysorbate, mannitol, dextran, modified polysaccharides and gums, phosolipids, and sulphobetains. The drug formulations, medications and/or active agents may also include fatty acids, castor oil, ethyl oleate and propylene glycol.

As used herein, the term active agent refers to an agent capable of treating, inhibiting and/or preventing a disorder or a disease. Exemplary active agents include pharmaceuticals and neutraceuticals. Preferred active agents are capable of treating, inhibiting and/or preventing a disorder or disease of one or more of the eyes, nose and throat.

It is important to note that while the exemplary pumping device described herein is based on an electromagnetic motive force any suitable motive force may be utilized. For example, motive forces may be provided by piezoelectric devices, electrostatic devices, thermopneumatic devices and electrochemical devices.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A lacrimal insert comprising: a punctal plug having a cavity therein; and a microelectromechanical pump and reservoir positioned within the cavity of the punctal plug, the microelectromechanical pump being configured to deliver at least one therapeutic dosage of an active agent contained in the reservoir into an eye of a patient on demand, the microelectromechanical pump and reservoir comprises a piston assembly including a magnetically actuatable piston configured to deliver a first dose of the at least one active agent upon application of a magnetic field to move the piston from a neutral position to an on position, and a second dose of the at least one active agent upon removal of the magnetic field and a biasing mechanism for returning the piston from the on position to the neutral position, two channels connecting the reservoir to outlets in the pump, and at least one valve cooperatively associated with the biasing mechanism to control the flow of the at least one active agent through the two channels.

2. The lacrimal insert according to claim 1, wherein the punctal plug comprises a collarette configured to rest on the exterior of a punctum, a bulb that projects into a canaliculus and a body portion connecting the collarette and the bulb, wherein the cavity is formed in at least a portion of the bulb and the body portion.

3. The lacrimal insert according to claim 2, wherein the punctal plug is fabricated from a thermoset elastomer.

4. The lacrimal insert according to claim 3, wherein the thermoset elastomer comprises silicone.

5. The lacrimal insert according to claim 4, further comprising a vent extending from the reservoir through the bulb of the punctal plug.

6. The lacrimal insert according to claim 5, wherein the microelectromechanical pump and reservoir are fabricated from silicon.

7. The lacrimal insert according to claim 6, wherein the piston assembly further comprises two static poles and one moveable pole, the piston being connected to the moveable pole.

8. The lacrimal insert according to claim 7, wherein the two static poles and one moveable pole comprise a magnetically conductive material.

9. The lacrimal insert according to claim 8, wherein the magnetically conductive material comprises iron and nickel.

* * * * *